United States Patent [19]

Niemann et al.

[11] 4,278,652

[45] Jul. 14, 1981

[54] PROCESS FOR DETERMINING FERRITIN

[75] Inventors: Elfriede Niemann, Kriftel, Fed. Rep. of Germany; Brian H. Stagg, Bletchley; Stuart I. Cowan, Marston Mortaine, both of England

[73] Assignee: Hoechst Aktiengesellschaft, Frankfurt am Main, Fed. Rep. of Germany

[21] Appl. No.: 954,897

[22] Filed: Oct. 26, 1978

[30] Foreign Application Priority Data

Oct. 29, 1977 [DE] Fed. Rep. of Germany ....... 2748657

[51] Int. Cl.$^3$ ..................... G01N 33/48; A61K 43/00; G01T 1/00
[52] U.S. Cl. ..................................... 424/1; 23/230 B; 424/12
[58] Field of Search ..................... 424/1, 12; 23/230 B

[56] References Cited

U.S. PATENT DOCUMENTS

| | | | |
|---|---|---|---|
| 2,955,074 | 10/1960 | Hink | 424/1 |
| 3,372,992 | 3/1968 | Storey et al. | 424/1 |
| 3,712,291 | 1/1973 | Freeman | 424/1 |
| 3,925,020 | 12/1975 | Ogawa et al. | 424/1 |

*Primary Examiner*—Benjamin R. Padgett
*Assistant Examiner*—Christine M. Nucker
*Attorney, Agent, or Firm*—Curtis, Morris & Safford

[57] ABSTRACT

A process for the determination of ferritin in serum or in plasma is disclosed, which comprises incubating an antibody directed against an organ-specific isoferritin, which is covalently bound to nylon(polyamide 6,6), on the one hand with ferritin standard solutions and on the other hand with serum samples, decanting or aspirating the incubation solutions, washing the nylon-antibody-ferritin complex formed and subsequently incubating it with a iodine-labelled antibody directed against a second organ-specific isoferritin, isolating the nylon-antibody-ferritin-anti-body-$^{125}$I-complex formed, counting its radioactivity in the gamma counter and comparing the standard samples with the serum samples.

2 Claims, No Drawings

PROCESS FOR DETERMINING FERRITIN

The present invention relates to a process for determining ferritin.

The assay of ferritin in serum of mammals, especially of humans, has been shown to provide a means of accurately assessing iron storage in the body.

According to J. W. Halliday et al. (cf. Clinica Chimica Acta 58, 207–214 (1975)) ferritin may be determined in serum using plastic tubes, which are coated inside with anti-liver ferritin antibodies. Either liver ferritin standards or serum samples are incubated, then after discarding the solution, washing the coating and treating it subsequently with anti-liver ferritin-$^{125}$I-antibodies and discarding the supernatant, the radioactivity bound to the coating in the tubes is counted in the gamma counter.

This procedure has the following disadvantages: Coating of the reaction tubes with antibodies in reproducible manner is extremely difficult. Furthermore, the layer of antibodies can be readily desorbed by serum or buffer. It is moreover sensitive, for example, to an excess or to a lack of humidity during storage. Finally, this process enables the quantitative determination of the ferritin of one organ only, while ferritins of other organs can be assessed only approximately by cross-reactions.

To avoid these disadvantages, a process has now been developed for the determination of ferritin in serum or plasma, which comprises incubating an antibody directed against an organ-specific isoferritin, which is covalently bound to polyamide 6,6, on the one hand with ferritin standard solutions containing an isoferritin identical with or different from that employed for producing the antibody, and on the other hand with serum samples under the same conditions, decanting or aspirating the incubation solutions, washing the polyamide 6,6-isoferritin specific antibody-ferritin complex formed and subsequently incubating it with a $^{125}$-I-labelled antibody directed against a second organ-specific isoferritin, which is different from the first one, decanting or aspirating the solution, washing the polyamide 6,6-antibody-ferritin antibody-$^{125}$I complex formed in which the antibodies are directed specifically against isoferritins of different organs, counting its radioactivity in the gamma counter and comparing the standard samples with the serum samples.

For performing the process according to the invention, ferritin is isolated on the one hand from human liver and on the other hand from human spleen according to one of the processes described in literature, for example according to R. Crichton (Structure Bonding 17, 68–139 (1973)) and purified subsequently. The organ is homogenized in distilled water and the homogenate is filtered by passing it through glass wool. After heating to 70° C. the filtrate is centrifuged and the supernatant is brought to 50% saturation with ammonium sulfate. The resulting precipitate as collected by centrifugation is dissolved in water and dialyzed against acetate buffer. After centrifugation the precipitate is dissolved in phosphate buffer solution. The resulting solution is chromatographed first on Sephadex$^R$ G 200 and then on Sepharose$^R$ 6B. The ferritin-containing fractions are collected and concentrated in an ultrafiltration cell.

Placental ferritin is isolated according to the method of H. Bohn (Archiv Gynecology 215, 263 (1973)).

The ferritin preparations are judged to be at least 95% pure by two-dimensional immunoelectrophoresis and isoelectric focussing.

Antibodies for coupling to polyamide 6,6 (nylon) are suitably raised in rabbits or preferably in sheep and antibodies for radiolabelling are raised in rabbits. For this purpose, each time 50 µg-2 mg of ferritin are used. The primary immunization involves injecting a solution of an isoferritin of one of said organs with the addition of Freund's adjuvant. The second immunization, which may be repeated, is carried out with isoferritin solutions, with the addition of Freund's adjuvant, if required.

After some weeks test bleeds are taken from the animals to isolate the antibodies from the serum either by precipitation with ammonium sulfate or by treatment with immunoabsorbants, for example cyanogen bromide-activated Sepharose 6 B.

The antibody thus isolated (immuno-gamma-globulin IgG) is covalently linked to polyamide 6,6 in the form of nets, rods or preferably beads, the latter having a diameter of a few millimeters, according to the method of H. Faulstich et al. (Federation of the European Biochemical Society Letters 48, 226 (1974)).

For radioactive labelling of the antibodies the serum obtained as described hereinbefore, preferably an antiplacental ferritin serum, is rendered specific by absorption on an immunoabsorbant, for example cyanogen bromide activated Sepharose 6 B coupled with placental ferritin, that is to say the portion of the placenta ferritin specific antibody is absorbed, for example on a column of said immunoabsorbant and subsequently eluted with diluted hydrochloric acid. Thus it is isolated. This specific antibody is radio iodine-labelled according to the method of Greenwood, Hunter and Glover (Biochem. Journal 89, 114 (1963)).

For preparing the isoferritin standards, the protein content of the individual isoferritins, derived from the liver, the spleen and the placenta is determined, according to the method of O. H. Lowry et al. (Journal of Biological Chemistry 193, 265 (1951)).

Ferritin standard solutions are obtained by diluting the isoferritins with a protein buffer solution, preferably horse serum, to concentrations between zero and 600 nanograms of ferritin per milliliter.

For determining ferritin in serum, a nylon particle, for example a nylon bead, to which an anti-isoferritin antibody (antibody directed against an organ-specific isoferritin, for example, derived from the spleen or liver) is linked covalently, is placed in a reaction tube and incubated for several hours, preferably 3–10 hours, at a temperature of from 20° to 40° C., with either 20–200 microliters µl of isoferritin standard solution, the isoferritin of which is identical with or different from that employed for the production of the antibody, or with 20–200 µl of patient's serum, the ferritin of which shall be determined, and with each of these 100–400 µl of borate buffer, preferably having a pH of about 8.6, which contains in addition to 0.2 to 1.0 weight percent of bovine serum albumin. Thereafter the solution is decanted or aspirated and the nylon-antibody-ferritin complex formed is washed with distilled water. Thereafter 200–400 µl of a solution of the radioiodine-labelled anti-isoferritin antibody (antibody directed against an organ-specific isoferritin, for example produced in placenta) are dispensed into each reaction tube and incubated for several hours, preferably of from 10 to 20 hours at a temperature of from 20° to 40° C.

Thereafter the solution is decanted or aspirated and the nylon-antibody-ferritin-antibody $^{125}$I complex formed is washed with distilled water. The radioactivity remaining bound to each nylon bead is counted in the gamma counter and the ferritin concentration of the serum samples is interpolated from the standard curve.

The following combinations, in particular the first three, are suitable for use in the process according to the invention:

| antibodies linked covalently to nylon | isoferritin standard | radioiodine-labelled antibody |
|---|---|---|
| anti-liver ferritin | spleen ferritin | anti-placental ferritin |
| " | liver ferritin | anti-spleen ferritin |
| " | " | anti-placental ferritin |
| " | placental ferritin | " |
| anti-spleen ferritin | liver ferritin | " |
| " | placental ferritin | " |
| " | spleen ferritin | " |
| " | placental ferritin | anti-liver ferritin |
| anti-placental ferritin | liver ferritin | " |
| " | " | anti-spleen ferritin |
| " | placental ferritin | " |
| " | spleen ferritin | " |

These combinations do not distinguish between the organ-specific isoferritins in serum. They are, consequently, suitable for determining the toal quantity of the isoferritins.

A combination of antibodies and standards of the above type enables the assay of the total serum ferritin, which is composed of the ferritins of single organs, down to 2 nanograms of ferritin per ml. The upper limit of the determination method is at about 400 nanograms of ferritin per ml. The values can be well reproduced. Higher ferritin values in serum up to 15,000 nanograms of ferritin per ml may also be determined when the serum to be determined is diluted with a serum free from human ferritin, for example horse serum.

For performing the process of the invention the reagents are suitably used as a kit which consists of the following components:
Receptacles containing
100 nylon beads to which anti-liver ferritin antibodies are bound,
1 anti-placental ferritin-$^{125}$I,
8 liver ferritin standards containing 0, 5, 10, 20, 40, 80, 160, 320 ng/ml,
1 test serum, the ferritin content of which is known,
1 dilution serum (horse serum),
1 buffer,
All reagents are lyophilized.
The following examples illutrate the invention:

EXAMPLES

1. Preparation of anti-liver ferritin antibodies

1. Immunization

Species: Sheep
A solution of 2 mg of liver ferritin in 2 ml of phosphate buffered saline of pH 7.4 is emulsified in 2 ml of Freund's adjuvant and injected intramuscularly at 4 to 5 sites. Test bleeds are taken at 7 to 10 day intervals and the titer of the antiserum is determined. On attaining a titer of 1:16 (Ouchterlony), a one liter bleed is taken from the animal to remove the serum therefrom.

1.2 Preparation of the IgG fraction of the antiserum

A saturated ammonium sulfate solution (536 g/l at 20° C.) is prepared and the pH adjusted to 7.4. To 100 ml of antiserum an equal volume of saturated ammonium sulfate solution is added with constant stirring. After stirring for 30 minutes at room temperature the material is centrifuged at 10,000 g for 10 minutes and the supernatant is discarded. The precipitate is dissolved in 50 ml of distilled water and transferred to a dialysis sac. Dialysis against distilled water at 4° C. is continued until the dialysate is free of sulfate ions. Dialysis is terminated after 16 to 24 hours. 3 to 4 changes of 3 l of distilled water are generally required.

The immunoglobulin solution obtained is lyophilized and stored at 4° C. in vacuo over silica gel. The yield of lyophilized material is aproximately 3.5 g of IgG/100 ml of antiserum.

2. Covalent coupling of anti-liver ferritin IgG to nylon beads 5,000 beads are washed in 1 l of carbon tetrachloride and allowed to dry. The dry beads are placed in the reaction vessel and 5 liters of 4.52 N HCl, cooled to room temperature, are added. The beads are stirred for 30 minutes, thereafter transferred to a Büchner funnel and washed with distilled water until free of acid. The beads are returned to the reaction vessel and 5 liters of 0.1 M $Na_2HPO_4$ solution are added. 100 g of succinic acid anhydride are added gradually, while the solution is maintained at a pH of 9.0 by the simultaneous dropwise addition of 46% NaOH. The batch is stirred for 4 hours at room temperature, the beads are again transferred to the Büchner funnel and washed successively with 5 liters of 50% acetic acid, 5 liters of distilled water and 1 l of dry dimethylformamide.

The following reactions must be performed under anhydrous conditions. The beads are returned to the reaction vessel and thereafter 5 l of dry dimethylformamide (DMF) are added. The vessel is placed in a cooling bath and the temperature of the reaction solution is reduced to $-15°$ to $-20°$ C. The beads are slowly stirred and 87 ml of triethylamine and 60 ml of ethylchloroformate are added. The batch is allowed to react for 15 minutes. The beads are then washed with 2 l of dry DMF and thereafter 75 g of N-hydroxysuccinimide dissolved in 2 l of dry DMF. After stirring for 1 hour at room temperature, the beads are washed with 5 l of cold distilled water. The beads are returned to the reaction bottle containing 2.5 l of the immunoglobulin solution and slowly rotated overnight at 4° C. (approximately 10 rpm). The immunoglobulin solution is decanted and replaced by 1 l of 1 M glycine solution. The beads are rotated for 30 minutes at room temperature in the glycine solution and washed thereafter with 5 l of borate-bovine serum albumin buffer. The beads are drained, placed as a mono-layer on a metal tray and dried overnight by lyophilization.

3. Production of anti-placental ferritin antibody 3.1 Immunization

Species: rabbit
A solution of 100 μg of placental ferritin in 1 ml of isotonic phosphate buffer solution of pH 7.4 is emulsified with 1 ml of Freud's adjuvant and injected intradermally at a number of sites.

Test bleeds are taken at 7 to 10 day intervals and the titer of the antiserum is determined by immunodiffusion against liver ferritin.

On attaining a titer of 1:4, a bleed of 50 ml is taken. The bleeds are repeated at 14 day intervals until the titer falls below 1:4.

All blood is allowed to clot and the serum is removed.

3.2 Preparation of the specific IgG 6.18 g of $H_3BO_3$ and 29.22 g of NaCl are dissolved in 900 ml of distilled water, the solution is titrated with NaOH to pH 8.6 and made up to 1 l with distilled water.

36 g of $Na_2HPO_4$ and 3.12 g of $Na_2H_2PO_4 \cdot 2 H_2O$ are dissolved in 1 l of distilled water. The pH of the solution is measured and adjusted to pH 7.4, if necessary.

A solution of 5 mg of placental ferritin is placed in a dialysis sac and dialyzed against two changes of 250 ml of borate/NaCl buffer of pH 8.6 overnight, at 4° C. The CNBr activated Sepharose ® (Pharmacia) is washed with 250 ml of 0.001 N HCl by gentle stirring in a sintered glass funnel. After allowing the Sepharose to drain, it is placed in a 25 ml screw top plastic universal bottle. The ferritin solution is removed from the dialysis sac, diluted with borate-NaCl buffer to 5 ml and transferred to the bottle containing the activated Sepharose. The contents of the bottle are gently mixed by end-over-end rotation for 2 hours at room temperature. Thereafter the resulting mixture is centrifuged at 7,000 rpm for 2 minutes to deposit the Sepharose. The supernatant is discarded and the Sepharose-ferritin immunoabsorbant is washed with $2 \times 10$ ml of borate-NaCl buffer, $2 \times 10$ ml of 0.005 N HCl and $2 \times 10$ ml of borate-NaCl-bovine serum albumin buffer.

The following operations are all performed at room temperature. The immunoabsorbant is packed into a column and the height of the liquid reservoir is adjusted to give a flow rate of 1 ml/2.5 minutes. The column is rinsed with borate/NaCl buffer. The supernatant liquid in the column is removed and 5 ml of anti-placental ferritin anti-serum are added. The antiserum is allowed to run through the column and unbound material is removed by washing the column with borate/NaCl buffer. 20 reaction tubes each containing 1 ml of 0.1 M phosphate buffer of pH 7.4 are placed in the fraction collector, the reservoir is charged with 0.005 N HCl and linked to the column. The fractions of the specific IgG which are eluted from the column are collected and stored at 4° C.

4. Iodination

Method

The specific anti-placental ferritin IgG is iodine-labelled with chloroamine T according to the method of Greenwood and Hunter (Biochem. J. 89 114 (1963)).

Product specification:
specific activity: 11 mCi/mg,
iodination degree: 1.0 atom of I/molecule
Purification: G-200 Sephadex column 0.05 M phosphate buffer of pH 7.4 plus 0.2% of bovine serum albumine.

5. Standards

A solution of 320 ng of liver ferritin/ml in horse serum is prepared. This stock solution is used as the starting point for a series of doubling dilutions giving standards of 160, 80, 40, 20, 10 and 5 ng of ferritin/ml. The zero standard consists of horse serum alone.

6. Performance of the ferritin determination

Sufficient polystyrene tubes are labelled in duplicate to accomodate eight standards, one test serum and a determinate number of patients' sera. In addition, tow reaction tubes are labelled for determining the total radioactivity.

One nylon bead is placed in each reaction tube (except the "total" tubes).

Thereafter 200 μl buffer solution are dispensed into each tube by means of a pipette.

Then, 100 μl of the standard solution, 100 μl of the test serum or 100 μl of the patients' samples are dispensed by a pipette into the reaction tubes prepared for this purpose.

The test tubes are briefly agitated on a vortex mixer and incubated for 5 hours at 37° C.

Thereafter the solutions are aspirated and the beads are washed with 2 ml of distilled water.

300 μl of the iodinated anti-placental ferritin solution are added to the nylon beads by means of a pipette, the reaction tubes are briefly agitated on a vortex mixer and incubated overnight at 37° C.

The solution is aspirated, the beads are washed with 2 ml of distilled water and the radioactivity is counted subsequently in a gamma counter.

For evaluating the results, the measured impulses of the eight standards are calculated as a percentage of the total activity. The percentage activity is plotted as ordinate against the ferritin concentration/ng/ml) as abscissa. The values plotted are linked to give a curve. The values of the test sera and of the patients' sera are interpolated from this curve.

What is claimed is:

1. A process for the determination of ferritin in serum or in plasma, which comprises incubating an antibody directed against a first organ-specific isoferritin, which is covalently bound to polyamide 6,6, on the one hand with ferritin standard solutions containing an isoferritin identical with or different from that employed for the production of the antibody, and on the other hand with serum samples under the same conditions, decanting or aspirating the incubation solutions, washing the polyamide 6,6-isoferritin specific antibody-ferritin complex formed and subsequently incubating it with a $^{125}$I-labelled antibody directed against a second organ-specific isoferritin, decanting or aspirating the solution, washing the polyamide 6,6-antibody-ferritin anti-body-$^{125}$I complex formed in which the antibodies are directed specifically against the isoferritins of different organs, counting its radioactivity in a gamma counter and comparing the standard samples with the serum samples.

2. The process as claimed in claim 1, in which the antibodies are produced against liver, spleen and placental ferritin and in which the standards consists of liver, spleen and placental ferritin.

* * * * *